United States Patent [19]

Belt et al.

[11] 4,420,078

[45] Dec. 13, 1983

[54] CARRYING CASE FOR A CARDIAC PACER

[75] Inventors: Kenneth W. Belt, Fort Atkinson; John S. Mattson, Milton, both of Wis.

[73] Assignee: Norland Corporation, Fort Atkinson, Wis.

[21] Appl. No.: 316,780

[22] Filed: Oct. 30, 1981

[51] Int. Cl.$^3$ .............................................. B65D 85/38
[52] U.S. Cl. ................................ 206/305; 150/52 R; 224/236; 224/253
[58] Field of Search ............... 224/163, 252, 253, 236; 206/37, 38, 45, 34, 305, 569, 570, 811; 128/419 P; 364/708; 312/7 R; 235/1 D; 455/351; 150/52 R

[56] References Cited

U.S. PATENT DOCUMENTS

| | | | |
|---|---|---|---|
| 2,096,376 | 10/1937 | Cauppe | 224/253 X |
| 2,826,523 | 3/1958 | Blaszkowski et al. | 150/52 R X |
| 3,314,464 | 4/1967 | Veilleux | 150/52 R |
| 4,071,065 | 1/1978 | Halbich | 150/52 R |

FOREIGN PATENT DOCUMENTS

| | | | |
|---|---|---|---|
| 4683 | 10/1979 | European Pat. Off. | 150/52 R |
| 2370450 | 7/1978 | France | 150/52 R |

*Primary Examiner*—William Price
*Assistant Examiner*—Gary E. Elkins
*Attorney, Agent, or Firm*—Lockwood, Dewey, Alex & Cummings

[57] ABSTRACT

A carrying case for a portable cardiac pacer having physician-actuable controls on the top and front panels of its housing includes a body portion having front, rear, side and bottom panels forming an open-ended enclosure in which the pacer is received. A first hinge-mounted flap extending across the open-end of the enclosure and a second hinge-mounted flap extending across the front panel of the body portion are secured at their free ends by a snap-fastener to the front panel of the body portion so as to retain the pacer securely seated within the enclosure. Each of the flap panels includes a rigid portion overlying the associated panel controls of the pacer to prevent inadvertent actuation of the controls by pressure applied externally to the carrying case.

13 Claims, 8 Drawing Figures

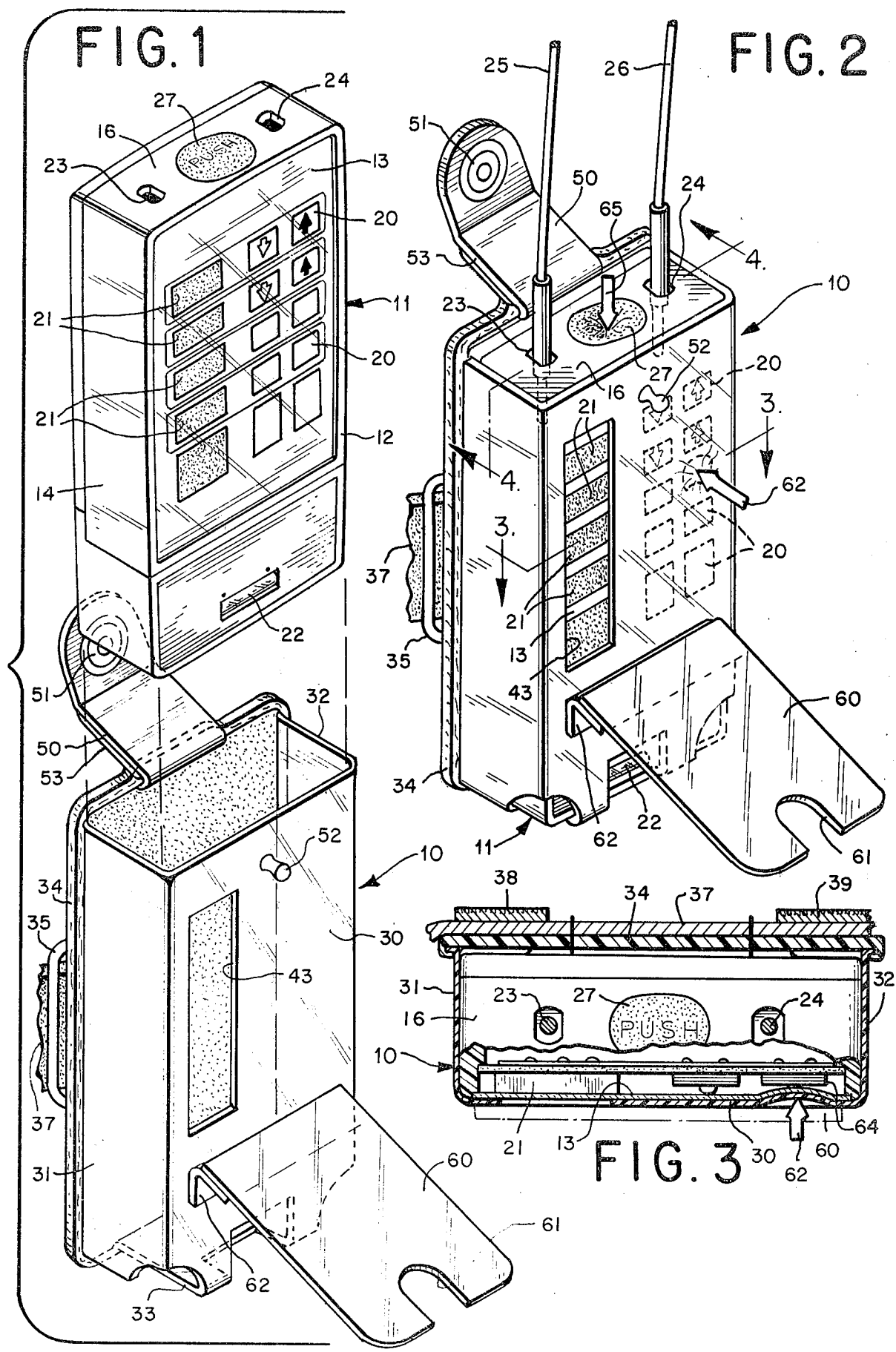

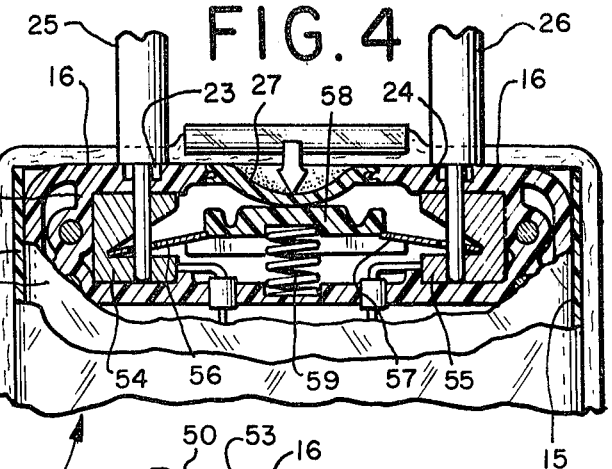
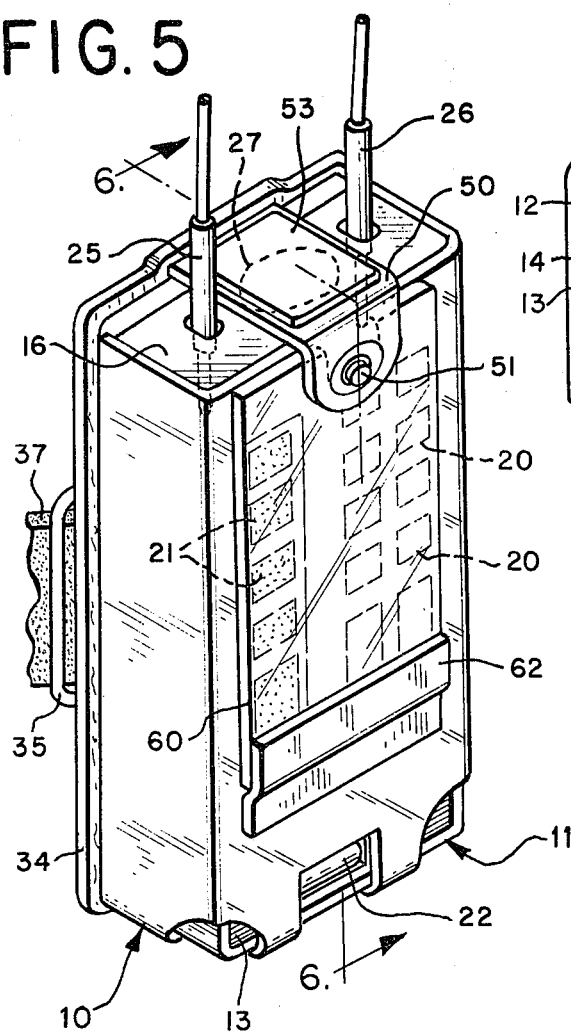
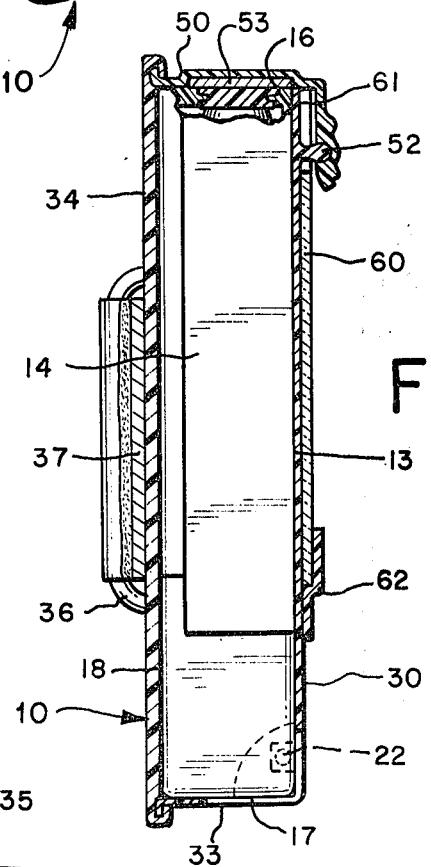
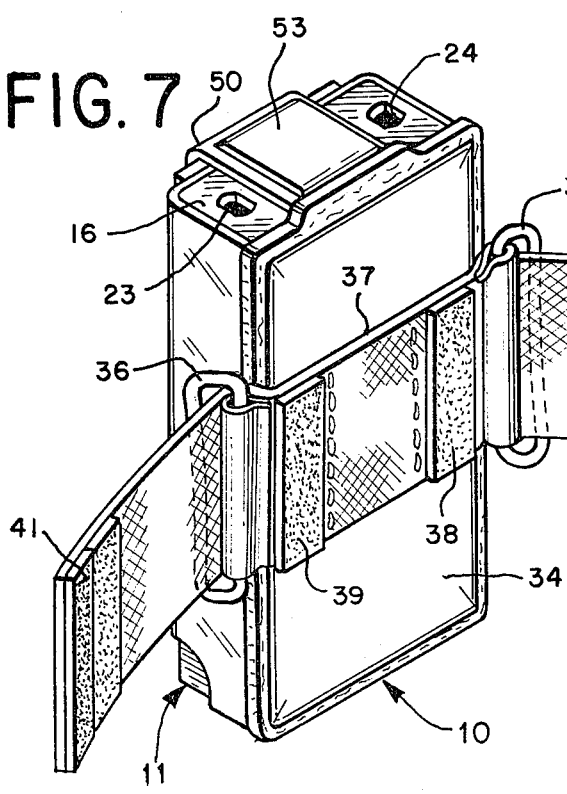
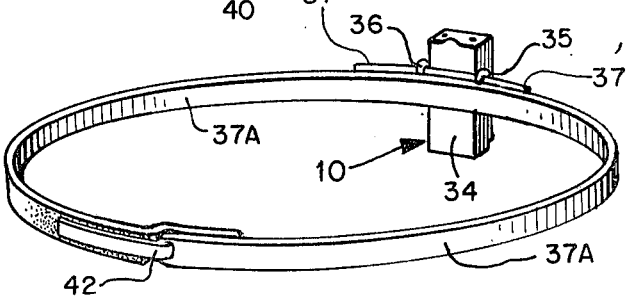

CARRYING CASE FOR A CARDIAC PACER

BACKGROUND OF THE INVENTION

The present invention is directed generally to portable cardiac pacer systems, and more particularly to a carrying case for a portable cardiac pacer.

Cardiac pacers, which supply amplitude and rate-controlled electrical pulses to a patient's heart to stimulate muscle contraction, have been developed for both internal applications, wherein the pacer is implanted within the patient's body, and external applications, wherein the pacer is externally carried by the patient and rate, pulse amplitude and sensitivity are adjusted as required by the application. External pacers are typically used in emergency situations, where the patient is awaiting implant of a permanent pacer, or where the operation of other pacers is being tested or adjusted. These pacers are typically battery powered for freedom of movement, and must be designed to provide a high degree of reliability in often adverse hospital and clinic environments.

External cardiac pacers respond to naturally occurring R-wave signals corresponding to ventricular contraction of the patient's heart by means of electrically conductive pacer leads which extend between the pacer and are physically attached to the heart. Stimulation pulses generated by the pacer are typically applied to the ventrical of the heart by the same leads to induce muscle contraction. In the course of operation of the portable pacer various operating parameters may be adjusted by the physician, including pacer sensitivity to applied R-wave signals, nominal operating rate and the amplitude of the stimulation pulses.

One problem encountered in the use of external pacers is providing an adequate arrangement for securing the pacer to the patient, both while the patient is in bed and while the patient is ambulatory. The method of attachment must be sufficiently secure so as to prevent the pacer from being pulled loose during movement of the patient, while allowing for ready-access to the pacer for adjustment of operating parameters, and for ready replacement of the pacer with another pacer should a failure occur.

Furthermore, the attachment arrangement should prevent inadvertent actuation of the pacer controls and consequent undesired variation in the pacer operating parameters while the pacer is in use and attached to a patient. However, the attachment must not unduly hinder access to the pacer controls by a physician in an emergency situation.

The present invention is directed to a carrying case for an external cardiac pacer which provides a secure means of attachment of the pacer to a patient and protection against inadvertent actuation of the controls of the pacer while the pacer is attached, while allowing the pacer to be readily adjusted and removed by a physician.

Accordingly, it is a general object of the present invention to provide a new and improved carrying case for a portable cardiac pacer.

It is a more specific object of the present invention to provide a carrying case for a cardiac pacer which provides an improved attachment of the pacer to a patient and improved protection against inadvertent actuation of the controls thereof, while allowing ready access to the pacer for adjustment or replacement.

SUMMARY OF THE INVENTION

A carrying case for use in conjunction with a portable cardiac pacer having a housing of generally rectangular cross-section having top, bottom, front, rear, left and right side panels, the front and top panels of the housing each including at least one physician-actuable control, includes a body portion including bottom, front, rear, left and right side walls and a top rim portion forming an enclosure having an interior cross-section generally corresponding to that of the pacer housing for receiving the housing, the top panel of the housing extending generally to the plane of the rim portion when the pacer is seated in the enclosure. A first flap panel extends from the rear panel to the front panel and over the physician-actuated top panel control, and is hingedly mounted to the body portion whereby the flap panel can be hinged away from the rim portion to allow actuation of the top panel control and removal of the cardiac pacer from the enclosure. A second flap panel extends over at least that portion of the front wall corresponding to the physician-actuated front panel control and substantially to the rim portion and is hingedly mounted to the body portion whereby the panel can be hinged away from the front wall to allow actuation of the front panel control. User-actuable fastener means fasten the free ends of the flap panels to each other and to the body portion whereby the cardiac pacer is retained in the enclosure and the physician-actuated controls are protected against inadvertent actuation by applied pressure from the exterior of the carrying case.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 1 is a perspective view of an external cardiac pacer system showing a cardiac pacer carrying case constructed in accordance with the invention and an external cardiac pacer for use therein.

FIG. 2 is a perspective view of the cardiac pacer carrying case of FIG. 1 with the flap panels thereof in an open position providing access to the pacer.

FIG. 3 is a top plan view of the pacer and carrying case of FIG. 2 partially broken away to illustrate a pressure switch on the front panel of the pacer.

FIG. 4 is a front elevational view of the top portion of the pacer and pacer carrying case of FIG. 2 partially broken away to show the pacer lead receptacle mechanism contained therein.

FIG. 5 is a perspective view of the pacer and pacer carrying case showing the panel flaps thereof in a closed position providing protection to the pacer against removal and unintentional adjustment.

FIG. 6 is a cross-sectional view of the pacer and pacer carrying case taken along line 6—6 of FIG. 5.

FIG. 7 is a rear perspective view of the pacer and pacer carrying case showing the strap arrangement provided therein for attaching the carrying case to a patient.

FIG. 8 is a rear perspective view of the pacer and pacer carrying case showing the use of a strap for attachment of the pacer to the arm or waist of a patient.

DESCRIPTION OF THE PREFERRED EMBODIMENT

Referring to the Figures, and particularly to FIG. 1, an external cardiac pacer system is shown having a pacer carrying case 10 of generally rectangular dimensions for receiving an external cardiac pacer 11.

The external cardiac pacer 11, which may be similar to that described in the copending application of Kenneth W. Belt, Ser. No. 203,959, filed Nov. 4, 1980, now abandoned, and assigned to the present assignee, comprises a housing 12 formed of a durable non-electrically conductive material, such as a high impact plastic. The housing 12 is generally rectangular in cross-section, and consists (as viewed in FIG. 1) of a front panel 13, a left side panel 14, a right side panel 15 (FIG. 4), a top panel 16, and a bottom panel 17 (FIG. 6). One or more of the panels may be formed as integral portions of the housing and the remaining panels may be tightly joined thereto to preclude the electronic circuitry within the housing from being exposed to spilled fluids and mechanical abuse.

The front panel 13 of the pacer housing includes a plurality of user-actuable pressure-sensitive switches 20 for varying the various operating parameters of the pacer. These switches, as described in the previously identified copending application, are actuated by inward deformation of a seamless front panel incorporated into the pacer housing. Appropriate indicia may be provided on the front panel to designate the pressure-responsive switch locations and the function of each switch. In addition, the front panel preferably includes a plurality of visual indicators 21, which may be liquid crystal display (LCD) type display devices visible from the exterior of the pacer housing. These readouts provide digital indications of the various operating parameters that have been set, as well as an indication of the operating mode of the pacer. An additional indicator 22 at the bottom of the front panel (as viewed in FIG. 1) may be provided to indicate remaining battery life.

Naturally occurring R-wave signals corresponding to ventricular contraction of the patient's heart are conveyed to the pacer by means of electrically conductive pacer leads physically attached to the heart. Stimulation pulses generated by the pacer are applied to the ventricle of the heart by the same leads to induce muscle contraction. To provide a connection for the pacer leads, pacer 11 includes a pair of pacer lead receptacles 23 and 24 on the top surface 16 of housing 12. The pacer leads 25 and 26 (FIG. 2) are inserted in receptacles 23 and 24 to establish the required electrical connections. One form of receptacle which provides a particularly good mechanically and electrically reliable connection is shown and described in the copending application of George L. Congdon, Ser. No. 210,276, filed Nov. 25, 1980, now U.S. Pat. No. 4,347,849, and assigned to the present assignee. This connector construction allows release of pacer leads 25 and 26 only upon depression of a release button 27, which is depressed by the physician only when substituting one pacer for another, or when replacing pacer wires, in which event the connection can be quickly released, without undue effort on the part of medical personnel, even under adverse lighting conditions.

The cardiac pacer carrying case 10 is seen to comprise a central body portion forming an open-ended enclosure of generally rectangular cross-section and of interior dimensions just slightly greater than the exterior dimensions of the housing 12 of cardiac pacer 11. The body portion includes, as shown in FIG. 1, a front wall 30, a left side wall 31, a right side wall 32, a bottom wall 33 and a rear or back wall 34.

The front wall 30, left sidewall 31, right sidewall 32 and bottom wall 33 are preferably formed of a relatively thin and flexible plastic sheet material such as vinyl. The rear or back wall 34 is preferably formed of a thicker and less resilient material so as to retain the enclosure formed by side walls 30-34 in the rectangular shape of the cardiac pacer 11 with which the carrying case 10 is intended for use. Attachment means comprising a strap segment 37 and a pair of D-shaped rings 35 and 36 (FIG. 7) fastened to the strap segment may be fastened to the rear wall 34 by stitching or other suitable means. Four pressure sensitive hook-and-loop type Velcro (trademark) fastener pads 38-41 (FIGS. 3 and 7) are preferably provided on the undersurface of strap segment 37 to enable the strap segment to be attached to a larger strap 37A encircling the arm or waist of the patient. The strap 37A which is preferably of sufficient length to encircle the arm or waist, may include a pressure-sensitive hook-and-loop type fastener strip 42 (FIG. 8) at one end to enable the bank to be drawn tight around the arm or waist.

To enable the readout devices 21 on the front panel 13 of the pacer to be viewed when the pacer is installed in carrying case 10 the front wall 30 of the carrying case is provided with an elongated rectangular window 43 which is in registration with the readout devices when the pacer is seated in the enclosure.

In accordance with the invention, carrying case 10 includes a first flap panel 50 for preventing the cardiac pacer 11 from being inadvertently moved or the pacer leads from being inadvertently released by actuation of release button 27 while the pacer is installed in the carrying case. As shown in FIGS. 1 and 2, flap panel 50 is hingedly attached by conventional means at one end to the rear wall 34 adjacent the rim portion of the enclosure. The flap panel includes at its free end a snap-fit fastener member 51 arranged for engagement with a mating snap-fastener member 52 mounted on the front wall 30 of the enclosure. When the snap-fit members are engaged, as shown in FIG. 5, flap panel 50 extends across the open rim portion of the enclosure so as to retain the cardiac pacer 11 securely in position within the enclosure.

In further accord with the invention, flap panel 50 includes a reinforcing plate 53 on its top surface which overlies release button 27 when flap panel 50 is secured to prevent inadvertent actuation of the button from pressure applied on the external surface of the flap panel. The reinforcing plate 53 may be secured to the flexible flap panel 50 by any appropriate means, such as by adhesive bonding, and an overlying vinyl coating may be applied to provide a finished appearance.

The construction of the receptacle assemblies 23 and 24 is shown in FIG. 4 to basically include a pair of terminal blocks 54 and 55 having bores within which the pins of respective ones of the pacer leads are received. Locking members in the form of flat plates 56 and 57 pivot within wedges on the sides of the connector blocks and engage the pacer lead pins so as to prevent removal of the pins from the connector blocks. The free ends of locking plates 56 and 57 engage respective sides of an actuator bar 58 mounted for reciprocative movement within housing 13 in a direction parallel to the axes of the connector pins. A spring 59 biases the actuator block toward the top of housing 13, wherein it is operatively engaged to actuator button 27.

Upon actuator buttom 27 being depressed, actuator bar 58 is forced downwardly against spring 59. This causes locking plates 56 and 57 to pivot within the wedges of connector blocks 54 and 55 such that they no longer engage pacer lead pins 25 and 26, allowing these pins to be pulled free of the connector blocks and the pacer.

In further accord with the invention carrying case 10 includes a second flap panel 60 hingedly attached at its lower end to the front wall 30 of the carrying case. Flap panel 60 is preferably relatively stiff and non-deformable, and is dimensioned to extend over that portion of the front panel occupied by the physician-actuable controls 20 and the readout devices 21, as shown in FIG. 5. A notch 61 in the upper or free end of the flap panel provides clearance for snap-fit connector portion 52 to extend beyond flap panel 60 and into engagement with its mating connector portion 51 on flap panel 50. In this way, as shown in FIGS. 5 and 6, the two flap panels 50 and 60 may be closed and secured by the single fastening means 51, 52. The bottom end of flap panel 60 is hinged to the top or front wall 30 of the carrying case by means of strip 62 of resilient material such as vinyl bonded along one edge to the housing and along the other edge to the flap panel.

When flap panel 60 is closed as shown in FIG. 5, the flap panel prevents the actuation of the front panel pacer controls 20 by reason of the stiff and non-deformable nature of the flap panel. The flap plate is preferably formed of a transparent material to allow the readout devices 21 to be read even with the flap panel closed. One form of acceptable material comprises a hard transparent plastic.

To make adjustments to the pacer, flap panel 50 is unbuttoned and flap panel 60 is folded down as shown in FIG. 2. Flap panel 50 may be snapped shut to prevent the pacer from sliding out of the carrying case enclosure. With flap panel 60 opened, controls 20 are readily actuated by applied pressure as shown by arrow 62 in FIG. 2. Appropriate indicia may be provided on the external surface of front wall 30 to facilitate the adjustment, or the front case may be further cut away to enable pressure to be applied directly to the front surface 13 of the pacer. With flap panel 60 closed, as shown in FIG. 5, pressure may be applied to the front surface without effect on the switches and the operation of the pacer.

With flap panel 50 closed, the non-deformable plate 53 incorporated therein prevents button 27 from being depressed, and thereby prevents the pacer leads 25 and 26 from being inadvertently removed. Furthermore, the flap panel 50 closed pacer 11 is prevented from sliding out through the open end of the carrying case enclosure.

As shown in FIG. 3, the force applied at 62 deforms the front panel 13 of the pacer sufficiently to actuate an underlying switch 64. As shown in FIG. 2, the application of force at 65 against release button 27 allows pacer leads 25 and 26 to be removed.

Carrying case 10 may be readily installed on the arm or waist of a patient by means of the attached strap 37. As shown in FIG. 8, this strap may be attached to a strap 37A by the pressure sensitive hook-and-loop type fastener pads 38–41 to provide a belt of sufficient girth to encircle the waist of a patient.

Thus, the carrying case of the invention provides improved security for a portable cardiac pacer while in use. By snapping free the top flap panel 50 of the carrying case access can be quickly gained to the pacer for the purpose of making adjustments, replacing the cardiac leads, or interchanging the pacer with another pacer. However, when the two flap panels are closed, the pacer is held securely in position and inadvertent release of the pacer leads or adjustment of the pacer operating parameters is precluded.

While a particular embodiment of the invention has been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

I claim:

1. A carrying case for use in conjunction with a portable cardiac pacer having a housing of generally rectangular cross-section having top, bottom, front, rear, left and right side panels, the front and top panels of the housing each including at least one physician-actuable control, said carrying case comprising:
   a body portion including bottom, front, rear, left and right side walls and a top rim portion forming an enclosure having an interior cross-section generally corresponding to that of the pacer housing for receiving the housing, the top panel of the housing extending generally to the plane of said rim portion when the pacer is seated in said enclosure;
   means including a first flap panel extending from said rear panel to said front panel and over said physician-actuated top panel control, said first flap panel being hingedly mounted to said body portion whereby said flap panel can be hinged away from said rim portion to allow actuation of said top panel control and removal of said cardiac pacer from said enclosure;
   means including a second flap panel extending over at least that portion of said front wall corresponding to said physician-actuated front panel control and substantially to said rim portion, said second flap panel being hingedly mounted to said body portion whereby said panel can be hinged away from said front wall to allow actuation of said front panel control; and
   user-actuable fastener means for fastening the free ends of said flap panels to each other and to said body portion whereby the cardiac pacer is retained in said enclosure and said physician-actuated controls are protected against inadvertent actuation by applied pressure from the exterior of the carrying case.

2. A carrying case for a cardiac pacer as defined in claim 1 wherein said physician-actuated controls are pressure actuated, and said flap panels each include a generally stiff portion overlying respective ones of said controls for preventing pressure-actuation thereof from the exterior of the carrying case.

3. A carrying case for a cardiac pacer as defined in claim 1 wherein said first and second flap portions are each hinge-mounted to said body portion so as to have a fold line generally parallel to the plane of said rim portion.

4. A carrying case for a cardiac pacer as defined in claim 3 wherein said fastener means include a first fastener portion on the front wall of said body portion, and a second fastener portion on the free end of said first flap panel, and wherein the free end of said second flap panel is received between said fastener portions.

5. A carrying case for a cardiac pacer as defined in claim 4 wherein said second flap panel includes a notch along the free end thereof to accommodate said fastener portions in locking engagement.

6. A carrying case for a cardiac pacer as defined in claim 4 wherein said fastener means comprise a snap fastener.

7. A carrying case for a cardiac pacer as defined in claim 1 wherein the housing further includes at least one visual indicator on the front panel thereof, and at least a corresponding section of said front wall of said body portion is cut away and at least a corresponding portion of said first flap panel is transparent to render said indicator viewable from the exterior of the carrying case.

8. A carrying case for a cardiac pacer as defined in claim 1 wherein the housing of the pacer includes at least one receptacle for receiving a connecting lead on the top panel thereof, said first flap panel is dimensioned to expose said receptacle to the exterior of said carrying case, and said physician-actuated control on the top surface comprises a pressure-actuated button for releasing said lead from said receptacle.

9. A carrying case for use in conjunction with a portable cardiac pacer having a housing of generally rectangular cross-section having top, bottom, front, rear, left and right side panels, the front and top panels of the housing each including at least one physician-actuable control, said carrying case comprising:

a body portion including bottom, front, rear, left and right side walls and a top rim portion forming an enclosure having an interior cross-section generally corresponding to that of the pacer housing for receiving the housing, the top panel of the housing extending generally to the plane of said rim portion when the pacer is seated in said enclosure;

means including a first flap panel extending from said rear panel to said front panel and including a rigid protective portion overlying said physician-actuated top panel control, said first flap panel being hingedly mounted to said body portion whereby said flap panel can be hinged away from said rim portion to allow actuation of said top panel control and removal of said cardiac pacer from said enclosure;

means including a second flap panel extending over at least a portion of said front wall substantially to said rim portion and including a rigid protective portion overlying said physician-actuated front panel control; said second flap panel being hingedly mounted to said body portion whereby said panel can be hinged away from said front wall to allow actuation of said front panel control; and user-actuable fastener means including a first fastener portion on the front wall of said body portion and a second fastener portion on the free end of said first flap panel, for fastening the free end of said first flap panel to said body portion, the free end of said second flap portion being retained therebetween whereby the cardiac pacer is retained in said enclosure and said physician-actuated controls are protected against inadvertent actuation by applied pressure from the exterior of the carrying case.

10. A carrying case for a cardiac pacer as defined in claim 9 wherein said second flap panel includes a notch along the free end thereof to accommodate said fastener portions in locking engagement.

11. A carrying case for a cardiac pacer as defined in claim 10 wherein said fastener means comprise a snap fastener.

12. A carrying case for a cardiac pacer as defined in claim 1 wherein the housing further includes at least one visual indicator on the front panel thereof, and at least a corresponding section of said front wall of said body portion is cut away and at least a corresponding portion of said first flap panel is transparent to render said indicator viewable from the exterior of the carrying case.

13. A carrying case for a cardiac pacer as defined in claim 9 wherein the housing of the pacer includes at least one receptacle for receiving a connecting lead on the top panel thereof, said first flap panel is dimensioned to expose said receptacle to the exterior of said carrying case, and said physician-actuated control on the top surface comprises a pressure-actuated button for releasing said lead from said receptacle.

* * * * *